US012673955B2

(12) United States Patent
Lu et al.

(10) Patent No.: US 12,673,955 B2
(45) Date of Patent: Jul. 7, 2026

(54) CRYSTAL FORM OF P-TOLUENESULFONATE SALT OF DIAZABICYCLIC COMPOUND AND PREPARATION METHOD THEREFOR

(71) Applicant: CRYSTAL PHARMATECH CO., LTD., Suzhou (CN)

(72) Inventors: Xia Lu, Suzhou (CN); Xiaoyu Zhang, Suzhou (CN)

(73) Assignee: CRYSTAL PHARMATECH CO., LTD., Suzhou (CN)

( * ) Notice: Subject to any disclaimer, the term of this patent is extended or adjusted under 35 U.S.C. 154(b) by 782 days.

(21) Appl. No.: 18/041,211

(22) PCT Filed: Jun. 8, 2021

(86) PCT No.: PCT/CN2021/098774
§ 371 (c)(1),
(2) Date: Feb. 9, 2023

(87) PCT Pub. No.: WO2021/249367
PCT Pub. Date: Dec. 16, 2021

(65) Prior Publication Data
US 2024/0018155 A1 Jan. 18, 2024

(30) Foreign Application Priority Data
Jun. 9, 2020 (CN) ........................ 202010515404.X

(51) Int. Cl.
*A61K 31/46* (2006.01)
*C07D 487/08* (2006.01)

(52) U.S. Cl.
CPC .................................. *C07D 487/08* (2013.01)

(58) Field of Classification Search
CPC .............................. A61K 31/46; C07D 487/08
See application file for complete search history.

(56) References Cited

U.S. PATENT DOCUMENTS 9,663,526 B2 5/2017 Fensome et al.

FOREIGN PATENT DOCUMENTS

CN 107074867 A * 8/2017 .............. A61P 37/06
TW 202045511 A 12/2020
(Continued)

OTHER PUBLICATIONS

English translation of CN 107074867 A, Pfizer, published Aug. 18, 2017, pp. 1-231. (Year: 2017).*
(Continued)

*Primary Examiner* — Amy L Clark
*Assistant Examiner* — Janet L Coppins
(74) *Attorney, Agent, or Firm* — MagStone Law, LLP; Enshan Hong

(57) ABSTRACT

The present disclosure relates to a novel crystalline form of a tosylate of diazadicyclic compound of formula (I), preparation method therefor, a pharmaceutical composition containing the crystal form, and the use of the crystal form in the preparation of a drug for treating alopecia areata, psoriasis and ulcerative colitis.

Formula (I)

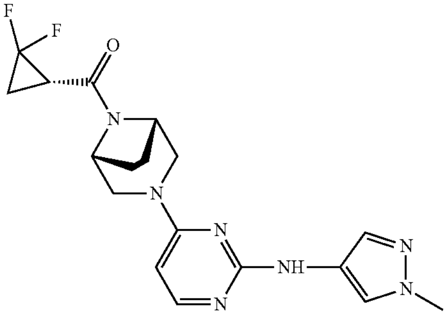

3 Claims, 11 Drawing Sheets

(56) References Cited

FOREIGN PATENT DOCUMENTS

| | | | | | |
|---|---|---|---|---|---|
| WO | WO-2016027195 | A1 * | 2/2016 | ................ | A61P 9/00 |
| WO | 2020165788 | A1 | 8/2020 | | |

OTHER PUBLICATIONS

International Search Report in PCT/CN2021/098774 mailed on Sep. 13, 2021, 9 pages.

Written Opinion in PCT/CN2021/098774 mailed on Sep. 13, 2021, 11 pages.

Tang, Xiaonan et al., Research Progress of Small-Molecule Drugs Targeting JAK in Autoimmune Diseases, Acta Pharmaceutica Sinica, 53(10): 1591-1597, 2018.

Andrew Fensome et al., Dual Inhibition of TYK2 and JAK1 for the Treatment of Autoimmune Diseases: Discovery of (( S)-2,2-Difluorocyclopropyl)((1 R,5 S)-3-(2-((1-methyl-1 H-pyrazol-4-yl)amino)pyrimidin-4-yl)-3,8-diazabicyclo[3.2.1] octan-8-yl)methanone (PF-06700841), Journal of medicinal chemistry, 53(10), 2018, 32 pages.

Andrew Fensome et al., Dual Inhibition of TYK2 and JAK1 for the Treatment of Autoimmune Diseases: Discovery of ((S)-2,2-Difluorocyclopropyl)((1R,5S)-3-(2-((1-methyl-1H-pyrazol-4-yl)amino)pyrimidin-4-yl)-3,8-diazabicyclo[3.2.1] octan-8-yl)methanone (PF-06700841), Journal of Medicinal Chemistry, 2018, 16 pages.

* cited by examiner

CRYSTAL FORM OF P-TOLUENESULFONATE SALT OF DIAZABICYCLIC COMPOUND AND PREPARATION METHOD THEREFOR

CROSS-REFERENCE TO RELATED APPLICATIONS

This application is a U.S. national stage under 35 U.S.C. § 371 of International Application No. PCT/CN2021/098774, filed on Jun. 8, 2021, which claims priority to Chinese Patent Application No. 202010515404.X, filed on Jun. 9, 2020, the contents of each of which are hereby incorporated by reference.

TECHNICAL FIELD

The present disclosure relates to the filed of chemical medicine, particularly relates to novel crystalline form of a tosylate salt of diazabicyclic compound and preparation method thereof.

BACKGROUND ((1S)-2,2-difluorocyclopropyl)((1R,5S)-3-(2-((1-methyl-1H-pyrazol-4-yl)amino)pyrimidin-4-yl)-3,8-diazabicyclo [3.2.1]octan-8-yl)methanone is a dual inhibitor of JAK1 and TYK2, which is useful for the treatment of certain inflammatory and autoimmune diseases. In particular, the compound is currently under clinic trials for the treatment of alopecia areata, psoriasis and ulcerative colitis and the structural formula is shown as the follows:

Formula (I)

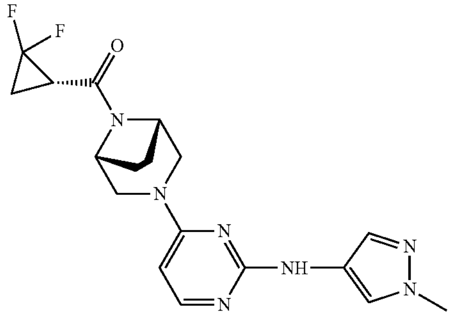

Formula (I) and its corresponding enantiomers were disclosed in U.S. Pat. No. 9,663,526B2. S configuration and the toyslate of S configuration is mainly used in the clinic trials (Andrew F., Catherine M. A. and et al, J. Med. Chem. 2018, 61, 8597-8612). However, there is no crystalline form of Formula (I) tosyalte disclosed so far.

Different crystalline forms of the same drug substance have differences in stability, solubility, safety, etc., which can affect drug's absorption and bioavailability. Therefore, it is one of the important research contents that cannot be ignored to carry out comprehensive and systematic polymorph screening in drug research and development, and select the most suitable crystalline form for development.

SUMMARY OF THE DISCLOSURE

The present disclosure is to provide novel crystalline of formula (I) tosylate, preparation method and uses thereof.

1. Crystalline form A of tosylate salt of formula (I) ((1S)-2,2-difluorocyclo-propyl) ((1R,5S)-3-(2-((1-methyl-1H-pyrazol-4-yl)amino)pyrimidin-4-yl)-3,8-diazabicyclo [3.2.1]octan-8-yl)methanone, named as tosylate Form A, wherein the X-ray powder diffraction pattern comprising characteristic peaks at 2θ values of 6.2°±0.2°, 18.6°±0.2°, 9.3°±0.2° using the Cu—Kα radiation, Formula (I)

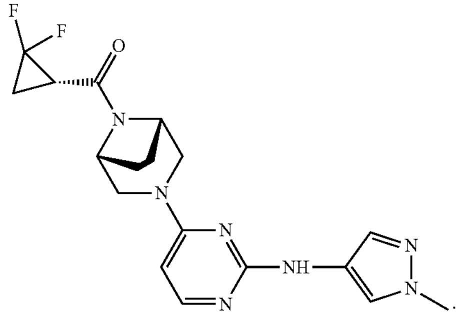

2. The X-ray powder diffraction pattern of said tosylate Form A according to item 1 comprises one or two or three characteristic peaks at 2θ values of 19.1°±0.2°, 14.1°±0.2°, 21.5°±0.2°.

3. The X-ray powder diffraction pattern of said tosylate Form A according to item 1 or 2 mentioned above comprises characteristic peaks at 2θ values of 19.1°±0.2°, 14.1°±0.2°, 21.5°±0.2°.

4. A process for preparing tosylate Form A according to any one of items 1 to 3, which comprises, Formula (I)

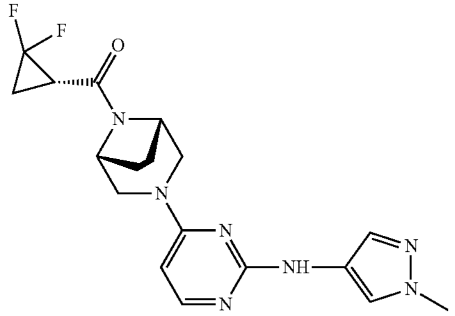

dissolving formula (I) tosylate into a solvent, filtering, and adding an anti-solvent into the filtrate dropwise to obtain tosylate Form A.

5. A process for preparing tosylate Form A according to any one of items 1 to 3, which comprises, Formula (I)

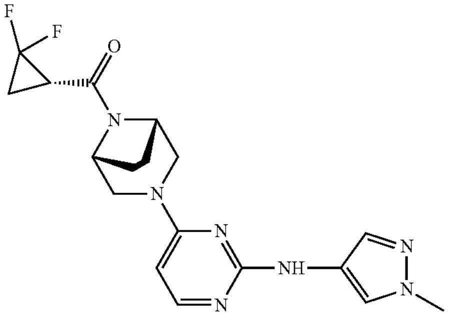

dissolving formula (I) tosylate into a solvent, filtering, and quickly adding the filtrate into an anti-solvent to obtain tosylate Form A.

6. A process for preparing tosylate Form A according to any one of items 1 to 3 which comprises, Formula (I)

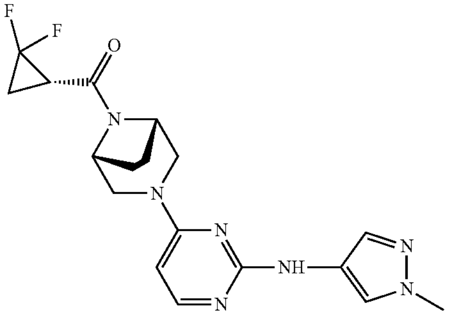

dissolving formula (I) tosylate into a volatile solvent and evaporating to obtain tosylate Form A.

7. A process for preparing tosylate Form A according to any one of items 1 to 3, which comprises, Formula (I)

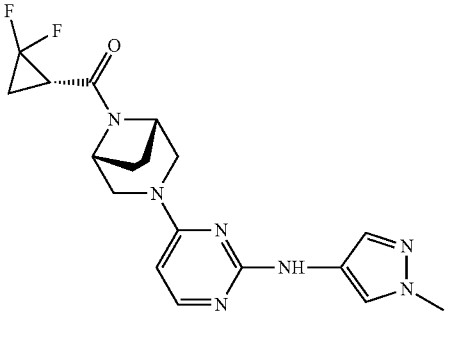

dissolving formula (I) tosylate into a solvent, placing the solution into a sealed environment containing an anti-solvent for liquid vapor diffusion to obtain tosylate Form A.

8. A process for preparing tosylate Form A according to any one of items 1 to 3, which comprises, Formula (I)

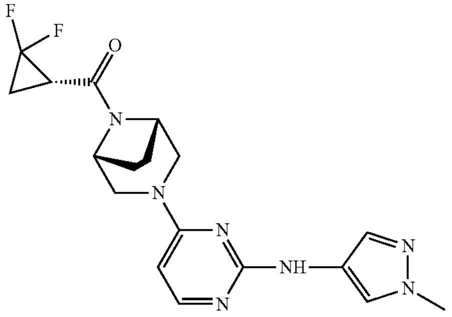

dissolving formula (I) tosylate into a solvent at a high temperature to reach dissolution quilibrium, filtering and cooling to obtain a solid and the obtained solid is tosylate Form A.

9. A pharmaceutical composition comprises the crystalline form according to any one of items 1 to 3 and pharmaceutically acceptable carriers.

10. A pharmaceutical composition that has JAK1 and TYK2 passway inhibitory activity, which contains the crystalline form according to any one of items 1 to 3 as an active component.

11. A prophylactic or curative drug for alopecia areata, psoriasis and ulcerative colitis, which contains the crystalline form according to any one of items 1 to 3 as an active component.

Compared with the prior art, tosylate Form A of formula (I) provided by the present disclosure have the advantages in at least one aspect of solubility, melting point, stability, dissolution, hygroscopicity, adhesion, flowability, bioavailability, processability, purification ability, formulation production, and safety, etc., which provides a new and better choice for the preparation of pharmaceutical formulations containing the JAK1 and TYK2 passway inhibitor, and is of great significance for the drug development.

DETAILED DESCRIPTION OF THE DISCLOSURE

Crystalline form A of tosylate salt of formula (I) ((1S)-2,2-difluorocyclo-propyl) ((1R,5S)-3-(2-((1-methyl-1H-pyrazol-4-yl)amino)pyrimidin-4-yl)-3,8-diazabicyclo[3.2.1]octan-8-yl)methanone, named as tosylate Form A, wherein the X-ray powder diffraction pattern comprises characteristic peaks at the 2θ values of 6.2°±0.2°, 18.6°±0.2°, 9.3°±0.2° using the Cu—Kα radiation, Formula (I)

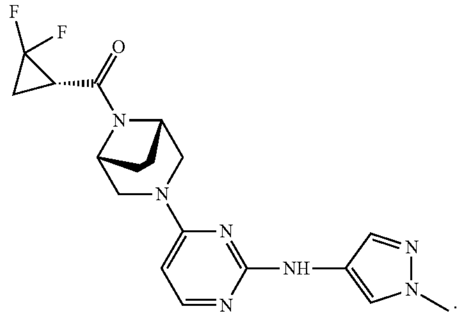

In an embodiment of the present disclosure, the X-ray powder diffraction pattern of tosylate Form A comprises one or two or three characteristic peaks at 2θ values of 19.1°±0.2°, 14.1°±0.2°, 21.5°±0.2°.

In an embodiment of the present disclosure, the X-ray powder diffraction pattern of tosylate Form A comprises characteristic peaks at 2θ values of 19.1°±0.2°, 14.1°±0.2°, 21.5°±0.2°.

In an embodiment of the present disclosure, the X-ray powder diffraction pattern of tosylate Form A comprises one or two or three characteristic peaks at 2θ values of 22.5°±0.2°, 19.8°±0.2°, 16.7°±0.2°.

In an embodiment of the present disclosure, the X-ray powder diffraction pattern of tosylate Form A comprises characteristic peaks at 2θ values of 22.5°±0.2°, 19.8°±0.2°, 16.7°±0.2°.

In an embodiment of the present disclosure, the X-ray powder diffraction pattern of tosylate Form A comprises at least four or five or six or seven or eight or nine characteristic peaks at 2θ values of 6.2°±0.2°, 18.6°±0.2°, 9.3°±0.2°, 19.1°±0.2°, 14.1°±0.2°, 21.5°±0.2°, 22.5°±0.2°, 19.8°±0.2°, 16.7°±0.2°.

In an embodiment of the present disclosure, the X-ray powder diffraction pattern of tosylate Form A comprises characteristic peaks at 2θ values of 6.2°±0.2°, 18.6°±0.2°, 9.3°±0.2°, 19.1°±0.2°, 14.1°±0.2°, 21.5°±0.2°, 22.5°±0.2°, 19.8°±0.2°, 16.7°±0.2°.

Figure 1:
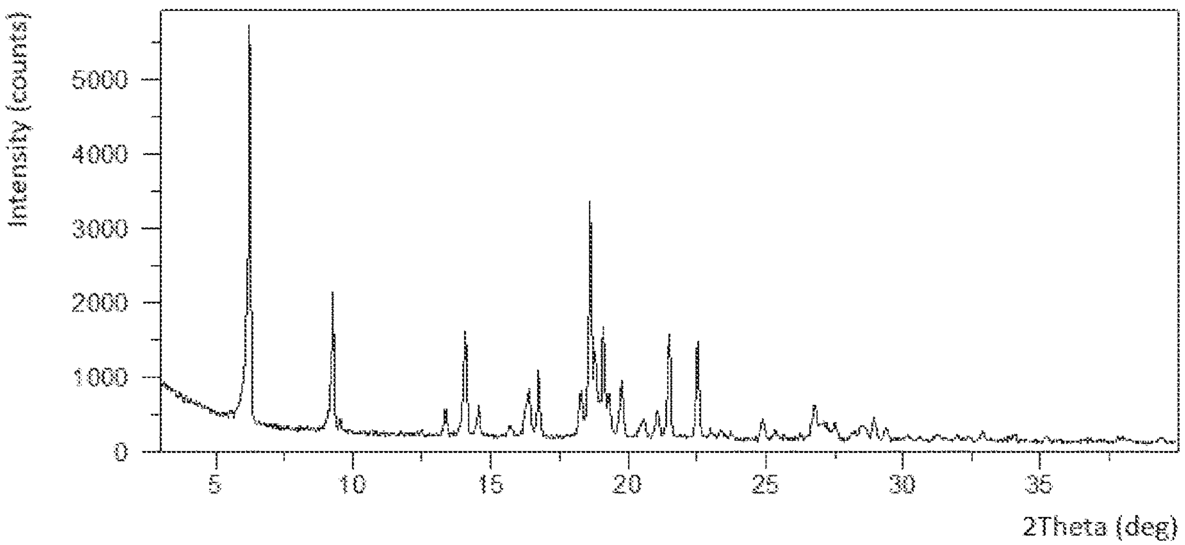
FIG. 1: XRPD pattern of tosylate Form A of example 1.

In an embodiment of the present disclosure, the X-ray powder diffraction pattern of tosylate Form A is depicted in FIG. 1.

A process for preparing tosylate Form A comprises: dissolving formula (I) tosylate into a solvent, filtering, and adding an anti-solvent into the filtrate dropwise to obtain tosylate Form A. Said solvent is methanol, dichloromethane, dimethylacetamide, dimethyl sulfoxide, or the mixture thereof, said anti-solvent is an ester, an alcohol, an ether, an alkane, an arene, or a ketone.

In an embodiment of the present disclosure, said ester is isopropyl acetate or ethyl acetate; Said alcohol is isopropanol; Said ether is methyl tert-butyl ether or tetrahydrofuran. Said alkane is n-heptane; Said arene is toluene; Said ketone is acetone.

In an embodiment of the present disclosure, the temperature of said adding an anti-solvent is 22° C. to 28° C.

A process for preparing tosylate Form A comprises: dissolving formula (I) tosylate into a solvent, filtering, and quickly adding the filtrate into an anti-solvent. If no solid precipitates, placing the system under a certain temperature until solid precipitates to obtain tosylate Form A. Said solvent is dichloromethane or dimethylacetamide; Said anti-solvent is an alcohol, an ether, an ester, or an arene.

In an embodiment of the present disclosure, said alcohol is isopropanol; Said ether is methyl tert-butyl ether or 2-methyltetrahydrofuran; Said ester is isopropyl acetate; Said arene is toluene.

In an embodiment of the present disclosure, said dissolving temperature is 22° C. to 28° C.

In an embodiment of the present disclosure, the filtrate is added into anti-solvent quickly with stirring.

In an embodiment of the present disclosure, the filtrate is added into anti-solvent at 22° C. to 28° C.

In an embodiment of the present disclosure, the solution is placed under a condition of −25° C. to −10° C., such as −20° C.

A process for preparing tosylate Form A comprises: dissolving formula (I) tosylate into a volatile solvent and evaporating to obtain tosylate Form A. The volatile solvent is an alcohol, a halohydrocarbon, an ether, an arene, water, or a solvent mixture thereof.

In an embodiment of the present disclosure, said alcohol is methanol, ethanol or isopropanol, preferably is methanol; Said halohydrocarbon is chloroform or dichloromethane; Said ether is tetrahydrofuran; Said arene is toluene.

In an embodiment of the present disclosure, said solvent mixture is selected from at least one type of methanol/toluene and tetrahydrofuran/water.

In an embodiment of the present disclosure, the volume ratio of methanol/toluene is 4:1. The volume ratio of tetrahydrofuran/water is 1:1.

In an embodiment of the present disclosure, the temperature of said dissolving and evaporating is 0° C. to 60° C., preferably 5° C. to 50° C.

In an embodiment of the present disclosure, after said filtering, high polymer is added to obtain tosylate Form A. Said high polymer is selected from at least one of polyvinylpyrrolidone, methylcellulose, polyvinyl alcohol, acrylic resin, carboxymethylcellulose sodium, 2-hydroxypropyl-β-cyclodextrin.

The mass ratio of said high polymer and formula (I) is 1:4-20, or 1:6-8.

A process for preparing tosylate Form A comprises: dissolving formula (I) tosylate into a good solvent, placing the solution into a sealed environment containing an anti-solvent for liquid vapor diffusion to obtain tosylate Form A.

In an embodiment of the present disclosure, said solvent is a single solvent or a mixture selected from methanol, toluene and ethanol. Said anti-solvent is methyl tert-butyl ether or acetone.

In an embodiment of the present disclosure, said solvent is selected from methanol/toluene or methanol/ethanol.

In an embodiment of the present disclosure, the volume ratio of methanol/toluene is 1-4:1, the volume ratio of methanol/ethanol is 1:1.

In an embodiment of the present disclosure, the temperature of said dissolving and diffusion is 20° C. to 30° C.

A process for preparing tosylate Form A comprises: dissolving formula (I) tosylate into a solvent at a high temperature, cooling to a low temperature for solid precipitation to obtain tosylate Form A. The solvent is a single solvent or a solvent mixture selected from methanol, ethanol, acetone.

In an embodiment of the present disclosure, said solvent mixture is methanol/acetone.

In an embodiment of the present disclosure, the volume ratio of methanol/acetone is 1:1.

In an embodiment of the present disclosure, said high temperature is 40° C. to 60° C.

In an embodiment of the present disclosure, said precipitation temperature is −20° C. to 5° C.

In an embodiment of the present disclosure, said cooling is a crash cooling.

In an embodiment of the present disclosure, rate of said cooling rate is 0.05° C./min to 0.5° C./min.

According to the present disclosure, the formula (I) and/or its tosylate as raw material refers to its solid (crystal or amorphous), semi-solid, wax or oil form. Preferably, the compound of formula (I) as raw material is in the form of solid powder. The "stirring" is completed by conventional methods in the art, such as magnetic stirring or mechanical stirring, and the stirring speed is 50-1800 rpm, wherein the stirring speed for the magnetic stirring is 300-900 rpm, and the stirring speed for the mechanical stirring is preferably 100-300 rpm.

In the present disclosure, "crystal" or "crystalline form" refers to the crystal or the crystalline form being identified by the X-ray diffraction pattern shown herein. Those skilled in the art are able to understand that physicochemical properties discussed herein can be characterized. The experimental errors depend on the instrument conditions, the sampling processes and the purity of samples. In particular, those skilled in the art generally know that the X-ray diffraction pattern typically varies with the experimental conditions. In particular, it is necessary to point out that, the relative intensity of the diffraction peaks in the X-ray diffraction pattern may also vary with the experimental conditions; therefore, the order of the diffraction peak intensities cannot be regarded as the sole or decisive factor. In fact, the relative intensity of the diffraction peaks in the X-ray powder diffraction pattern is related to the preferred orientation of the crystals, and the diffraction peak intensities shown herein are illustrative and absolute comparison is not required. In addition, the experimental error of the diffraction peak position is usually 5% or less, and the error of these positions should also be taken into account. An error of ±0.2° is usually allowed. In addition, due to experimental factors such as sample thickness, the overall offset of the diffraction peak is caused, and a certain offset is usually allowed. Thus, it will be understood by those skilled in the art that a crystalline form of the present disclosure is not necessarily to have the exactly same X-ray diffraction pattern of the example shown herein and the "X-ray powder diffraction pattern is same" as described herein is not meaning absolutely the same, the same peak position can differ by ±0.2° and the peak intensity allows for some variability. Any crystalline forms whose X-ray diffraction patterns have the same or similar characteristic peaks should be within the scope of the present disclosure. Those skilled in the art can compare the patterns shown in the present disclosure with that of an unknown crystalline form in order to identify whether these two groups of patterns reflect the same or different crystalline forms.

In some embodiments, tosylate Form A of the present disclosure is pure, single, and substantially free of any other crystalline forms. In the present disclosure, the term "substantially free" when used to describe a novel crystalline form, it means that the content of other crystalline forms in the novel crystalline form is less than 20% (w/w), specifically less than 10% (w/w), more specifically less than 5% (w/w) and further more specifically less than 1% (w/w).

It should be noted that a numerical value and a numerical range in the present disclosure should not be narrowly understood as the numerical value itself or the numerical range itself. It should be understood by those skilled in the art that the specific numerical value can be floated according to the specific technical environment on the basis of not departing from the spirit and principle of the present disclosure. In the present disclosure, the number of floating ranges which can be expected by one of skilled in the art is represented by the term "about".

The upper limit value and the lower limit value of the numerical range described in the specification of the present disclosure can be arbitrarily combined.

EXAMPLES

The following will further illustrate the present disclosure through specific examples, which are not intended to limit the protection scope of the present disclosure. Those skilled in the art can make improvements to the preparation processes and the used instruments within the scope of the claims, and those improvements should be considered as falling into the protection scope of the present disclosure. Therefore, the protective scope of the present disclosure should be defined by the appended claims.

In the present disclosure, "room temperature" generally refers to 22° C. to 28° C., unless otherwise specified.

The abbreviations used in the present disclosure are explained as follows:

XRPD: X-ray Powder Diffraction

DSC: Differential Scanning calorimetry

TGA: ThermoGravimetric Analysis $^{1}$H NMR: Proton Nuclear Magnetic Resonance

X-ray powder diffraction patterns of the present disclosure were acquired by Empyrean-Type and X'Pert$^3$-Type X-ray powder diffractometers of Panalytical Corporation. The parameters of X-ray powder diffraction of the present disclosure were as follows:

X-ray source: Cu, Kα

Kα1 (Å): 1.540598; Kα2 (Å): 1.544426

Kα2/Kα1 intensity ratio: 0.50

Voltage: 45 kilovolts (kV)

Current: 40 milliamps (mA)

Scanning range: from 3.0 to 40.0 degrees (2θ value).

Differential scanning calorimetry analysis charts of the present disclosure were acquired by a Q2000-type and Discovery Q2500-type differential scanning calorimeters of TA Company. The parameters of the differential scanning calorimetry analysis of the present disclosure were as follows:

Scanning rate: 10° C./min

Protection gas: Nitrogen.

The thermogravimetric analysis charts of the present disclosure were acquired by Discovery 5500-type and Q5000-type thermogravimetric analyzers of TA Company. The parameters of the thermogravimetric analysis of the present disclosure were as follows:

Scanning rate: 10° C./min

Protection gas: Nitrogen.

The dynamic vapor sorption diagrams of the present disclosure were collected on Intrinsic-type and Intrinsic Plus-type dynamic vapor sorption instruments of SMS company. The parameters of the dynamic vapor sorption test of the present disclosure were as follows:

Temperature: 25° C.

Protection gas and flow rate: $N_2$, 200 m L/min dm/dt: 0.002%/min

Minimum dm/dt equilibration time: 10 min

Maximum Equilibration Time: 180 min

Relative humidity range: 0% RH-95% RH-0% RH

Relative humidity gradient: 10% (0% RH-90% RH-0% RH), 5% (90% RH-95% RH and 95% RH-90% RH).

The particle size distribution results of the present disclosure were collected on S3500-type laser particle size analyzer of the Microtrac company. The Microtrac S3500 was equipped with an SDC (Sample Delivery Controller) sampling system. The wet method was used in this test, using Isopar G (containing 0.2% lecithin) as the test dispersion medium. The process parameters of the laser particle size analyzer were as follows.

| | |
|---|---|
| Particle size distribution: volume distribution | Acquisition time: 10 seconds |
| Dispersion medium: Isopar G | Particle size coordinate: Standard |
| Collection times: 3 times | Refractive index of dispersion medium: 1.42 |
| Transparency: Transparent | Residuals: Enabled |
| Particle refractive index: 1.59 | Flow rate: 60%* |
| Particle shape: Irregular | Filtration: Enabled |
| Ultrasonication power: 30 W | Ultrasonication time: 30 seconds |

*Flow rate 60% was 60% of 65 mL/s.

The intrinsic dissolution rate data of the present disclosure were collected on an Agilent 708DS-type dissolution apparatus of the Agilent company. The intrinsic dissolution test conditions were as follows.

| Dissolution apparatus | Agilent 708DS |
|---|---|
| Method | Paddle |
| Medium | pH 6.8 Phosphate Buffer |
| Medium volume | 900 mL |
| Rotation speed | 100 rpm |
| Medium temperature | 37° C. |
| Sampling points | 1, 2, 3, 4, 5, 10, 15, 20, 25, 30 minutes |
| Supplemental medium | No |

The polarized light microscope photos of the present disclosure were taken at room temperature with a Zeiss microscope Axio Scope.A1 equipped with an Axiocam 305 color camera and 5×, 10×, 20× and 50× objective lenses.

The starting material of formula (I) and/or tosylate salt thereof used in the following examples were prepared according to the methods in the prior art, and the crystalline form of starting material is not the key factor for preparation the crystalline form of the present disclosure.

Example 1: Preparation of Tosylate Form A 10.1 mg of formula (I) tosyalate solid was added into a 3-mL vial at room temperature, and then 1.0 mL of methanol was added to form a suspension. After the suspension was magnetically stirred at 50° C. (1000 rpm) for about 2 hours, the suspension was filtered into a new 3-mL vial using 0.45 μm PTFE filter membrane. The vial was sealed and then placed under −20° C. to obtain solid.

Figure 2:
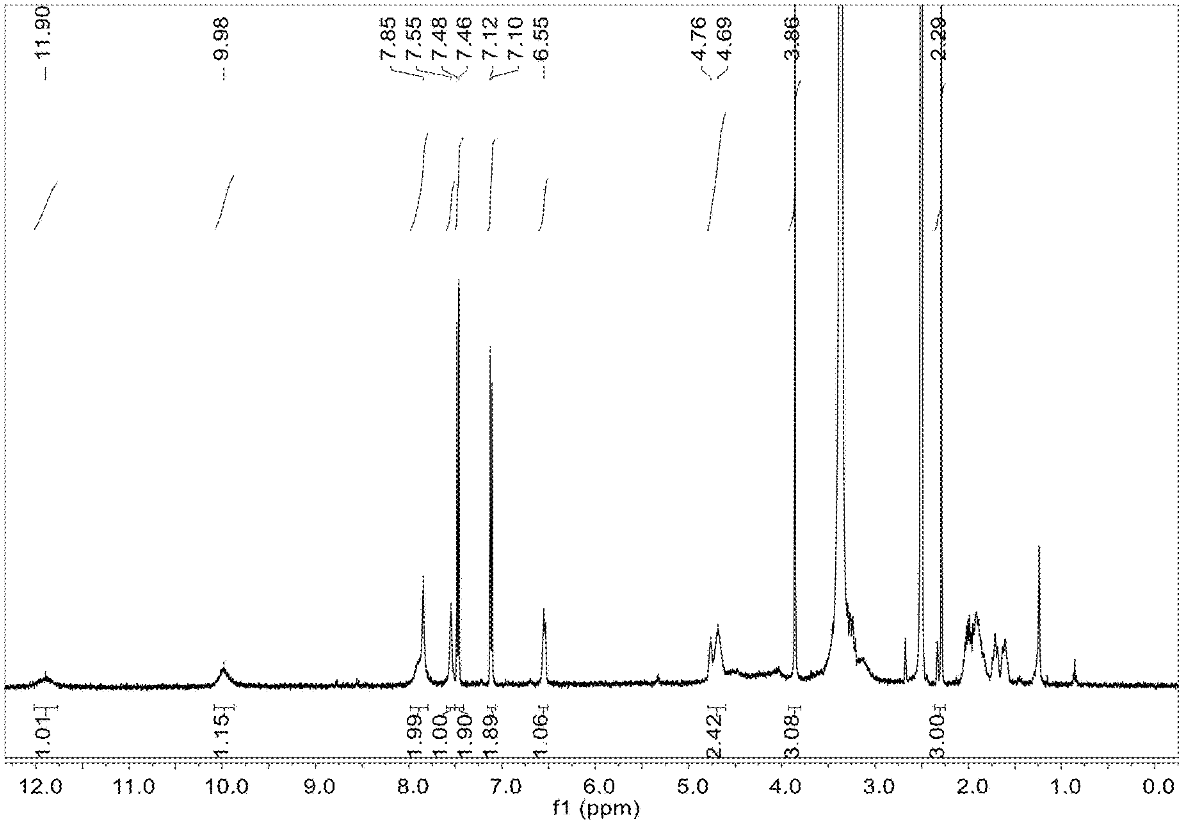
FIG. 2: 1H NMR spectrum of tosylate Form A of example 1.

The obtained solid was determined to be tosylate Form A after characterization. The XRPD pattern of tosylate Form A was shown in FIG. 1, and the corresponding XRPD data was summarized in Table 1. The $^1$H NMR spectrum was shown in FIG. 2, and stoichiometric ratio of freeform/p-toluenesulfonic acid was 1:1, with no solvent residual detecting.

TABLE 1

| Pos. [°2θ] | d-Spacing [Å] | Rel. Int. [%] |
|---|---|---|
| 6.22 | 14.21 | 100.00 |
| 9.27 | 9.54 | 34.72 |
| 9.54 | 9.28 | 3.27 |
| 13.37 | 6.62 | 7.10 |
| 14.07 | 6.29 | 27.56 |
| 14.56 | 6.09 | 7.68 |
| 15.70 | 5.64 | 3.03 |
| 16.38 | 5.41 | 12.45 |
| 16.74 | 5.30 | 16.26 |
| 18.29 | 4.85 | 12.18 |
| 18.63 | 4.76 | 64.75 |
| 18.80 | 4.72 | 17.93 |
| 19.11 | 4.65 | 29.96 |
| 19.31 | 4.60 | 12.11 |
| 19.77 | 4.49 | 15.22 |
| 20.57 | 4.32 | 4.47 |
| 21.07 | 4.22 | 7.34 |
| 21.49 | 4.13 | 27.06 |
| 22.53 | 3.95 | 25.01 |
| 23.02 | 3.86 | 1.94 |
| 23.39 | 3.80 | 2.09 |
| 24.88 | 3.58 | 4.81 |
| 25.35 | 3.51 | 2.26 |
| 26.29 | 3.39 | 1.78 |
| 26.79 | 3.33 | 9.28 |
| 27.10 | 3.29 | 4.72 |
| 27.51 | 3.24 | 4.64 |
| 28.14 | 3.17 | 2.02 |
| 28.55 | 3.13 | 3.73 |
| 28.96 | 3.08 | 6.29 |
| 29.38 | 3.04 | 3.42 |
| 30.18 | 2.96 | 1.17 |
| 30.59 | 2.92 | 0.84 |
| 31.29 | 2.86 | 1.48 |
| 31.96 | 2.80 | 1.50 |
| 32.35 | 2.77 | 1.13 |
| 32.89 | 2.72 | 2.24 |
| 34.02 | 2.64 | 1.79 |
| 35.23 | 2.55 | 1.23 |
| 36.81 | 2.44 | 0.51 |
| 37.98 | 2.37 | 1.17 |
| 39.40 | 2.29 | 1.11 |

Example 2: Preparation of Tosylate Form A 6.2 mg of formula (I) tosylate solid was weighed into a 3-mL glass vial at room temperature, and then 1.0 mL of methanol/toluene (1:1, v/v) was added. The mixture was filtered into a new 3-mL glass vial using 0.45 μm PTFE filter membrane. The vial was placed into a 20-mL vial with 3 mL of methyl tert-butyl ether. The vial was kept at room temperature for about two weeks to obtain solid.

Figure 3:
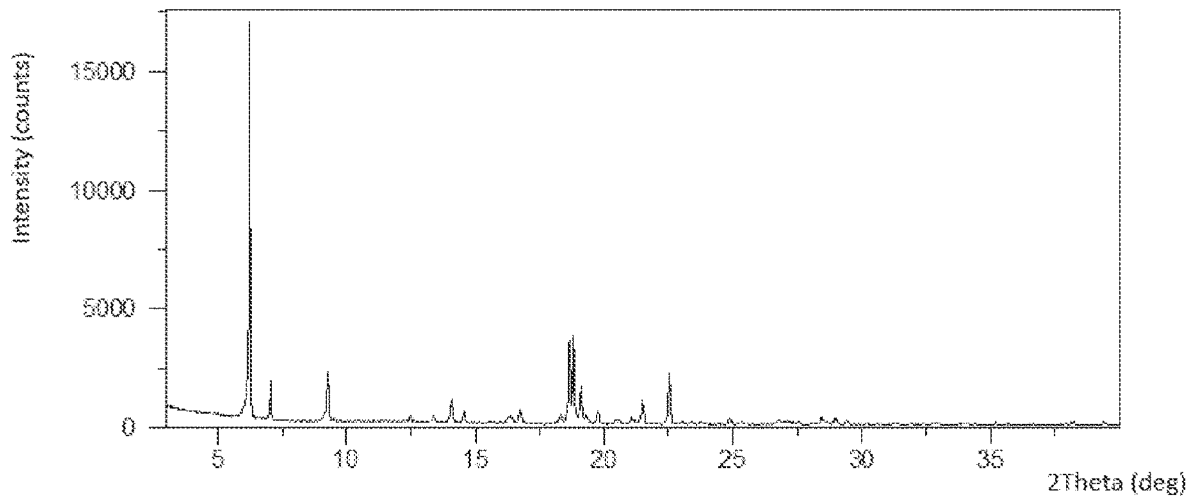
FIG. 3: XRPD pattern of tosylate Form A of example 2.
Figure 4:
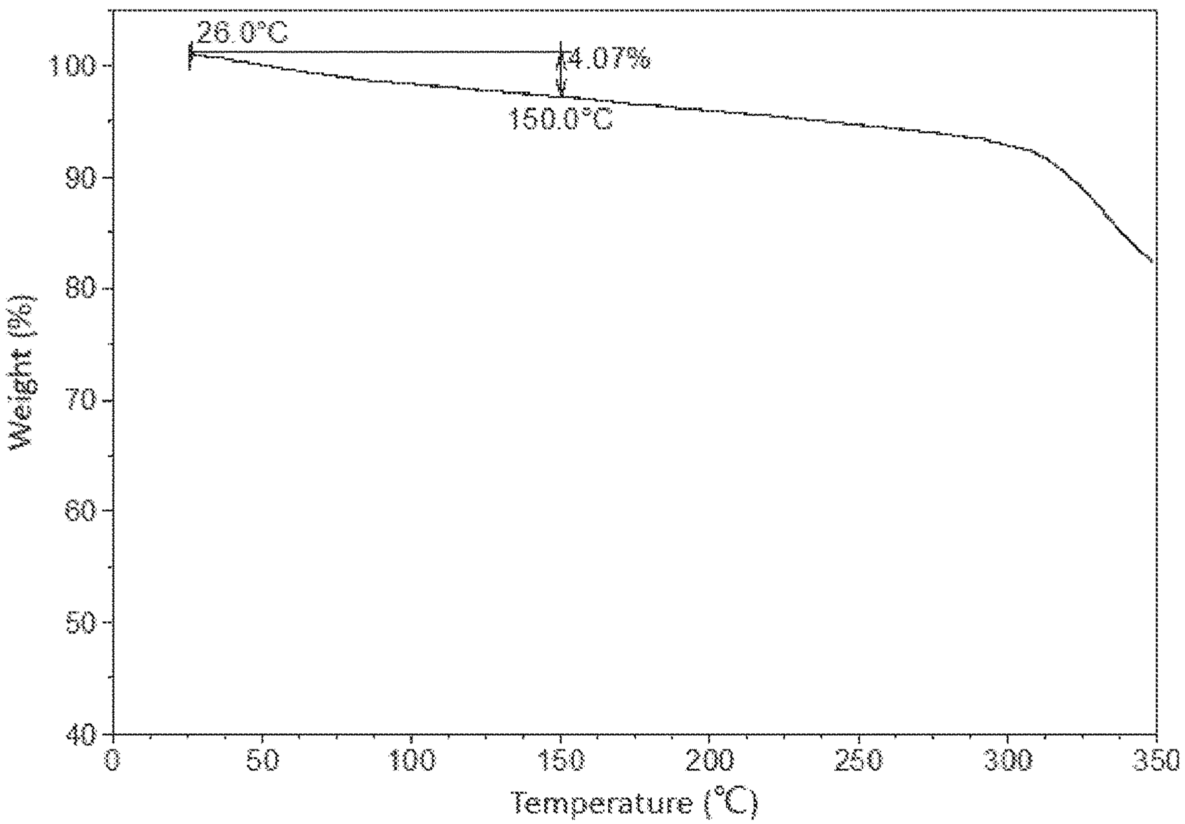
FIG. 4: TGA curve of tosylate Form A of example 2.
Figure 5:
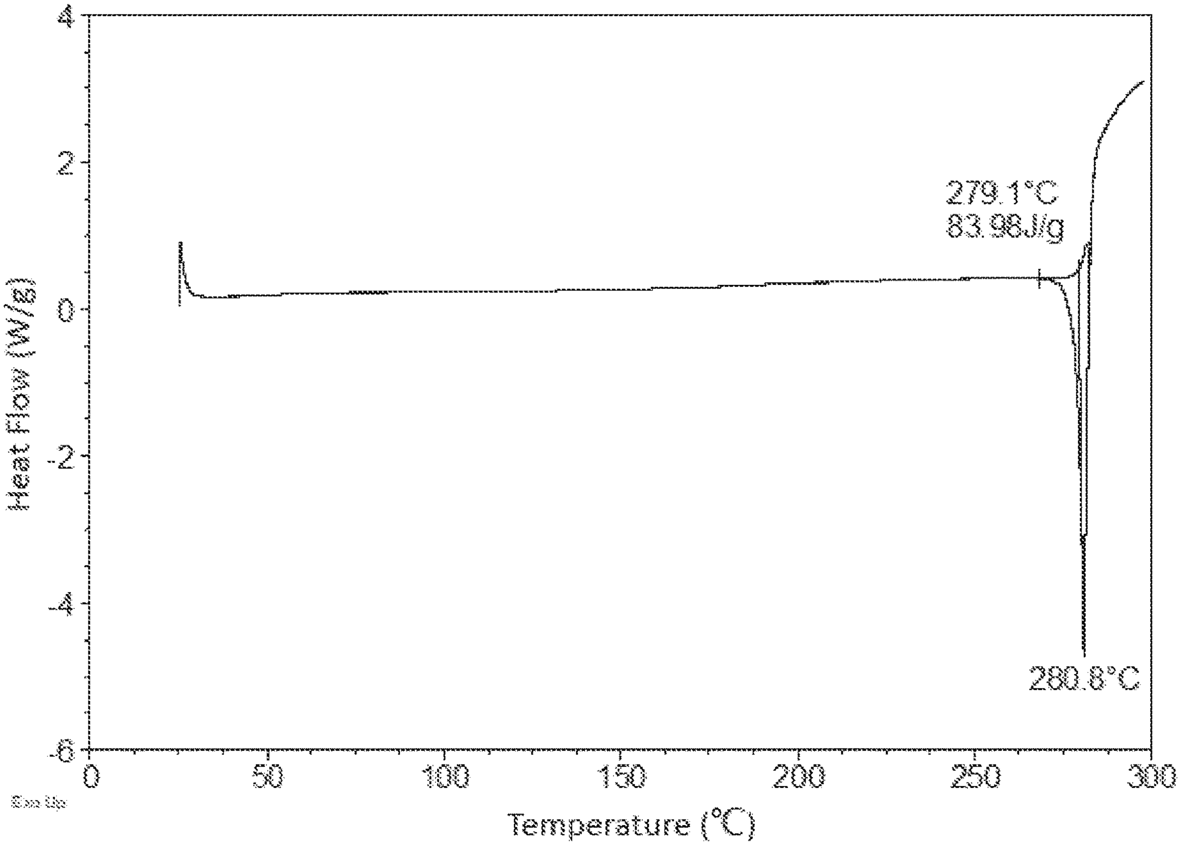
FIG. 5: DSC curve of tosylate Form A of example 2.

The obtained solid was determined to be tosylate Form A after characterization. The XRPD pattern of tosylate Form A was shown in FIG. 3, and the corresponding XRPD data was summarized in Table 2. The TGA curve was shown in FIG. 4, and the DSC curve was shown in FIG. 5, showing that the melting point was about 280° C. Combined with the characterization results, tosylate Type A was speculated to be an anhydrate.

TABLE 2

| Pos. [°2θ] | d-spacing [Å] | Rel. Int. [%] |
|---|---|---|
| 6.22 | 14.20 | 100.00 |
| 9.27 | 9.54 | 7.55 |
| 9.53 | 9.28 | 1.28 |
| 12.48 | 7.09 | 1.58 |
| 13.36 | 6.63 | 2.18 |
| 14.14 | 6.26 | 1.08 |
| 14.56 | 6.09 | 1.76 |
| 15.58 | 5.69 | 0.21 |

TABLE 2-continued

| Pos. [°2θ] | d-spacing [Å] | Rel. Int. [%] |
|---|---|---|
| 16.28 | 5.45 | 1.15 |
| 16.73 | 5.30 | 3.05 |
| 18.28 | 4.85 | 0.46 |
| 18.64 | 4.76 | 11.74 |
| 18.79 | 4.72 | 15.26 |
| 19.12 | 4.64 | 7.77 |
| 19.82 | 4.48 | 0.47 |
| 20.49 | 4.34 | 0.41 |
| 21.49 | 4.13 | 6.09 |
| 22.53 | 3.95 | 11.47 |
| 22.97 | 3.87 | 0.84 |
| 23.74 | 3.75 | 0.43 |
| 24.86 | 3.58 | 0.65 |
| 25.28 | 3.52 | 0.39 |
| 26.62 | 3.35 | 0.29 |
| 28.18 | 3.17 | 0.41 |
| 28.53 | 3.13 | 0.39 |
| 28.95 | 3.08 | 1.94 |
| 29.40 | 3.04 | 0.73 |
| 32.92 | 2.72 | 0.50 |
| 34.01 | 2.64 | 0.23 |
| 35.17 | 2.55 | 0.22 |
| 38.13 | 2.36 | 0.54 |
| 39.40 | 2.29 | 0.54 |

Example 3~4: Preparation of Tosylate Form A (Liquid Vapor Diffusion)

Appropriate amount of formula (I) tosylate solid was weighed into a 3-mL glass vial, and then corresponding solvent was added to dissolve the solid. The mixture was filtered into a new 3-mL glass vial using 0.45 μm PTFE filter membrane. The vial was placed into a 20-mL vial with 3 mL of anti-solvent. The vial was kept at room temperature for about two weeks to obtain solid. If no solid was obtained, the solution was transferred to slow evaporation at room temperature.

The obtained solid was determined to be tosylate Form A after characterization. The detailed procedure was shown in Table 3, and the XRPD data of example 3 was summarized in Table 4.

TABLE 3

| | | Solvent | | Anti-solvent | | |
|---|---|---|---|---|---|---|
| Example | Mass (mg) | Type (v/v) | Volume (mL) | Type | Volume (mL) | Condition |
| 3 | 3.3 | Methanol/ toluene (4/1) | 0.5 | Acetone | 3.0 | Liquid vapor diffusion |
| 4 | 3.0 | Methanol/ ethanol (1/1) | 0.8 | Methyl tert-butyl ether | 3.0 | Liquid vapor diffusion |

TABLE 4

| Pos. [°2θ] | d-spacing [Å] | Rel. Int. [%] |
|---|---|---|
| 6.22 | 14.22 | 100.00 |
| 9.28 | 9.53 | 9.19 |
| 12.48 | 7.09 | 1.37 |
| 13.35 | 6.63 | 1.86 |
| 14.11 | 6.28 | 0.93 |
| 14.58 | 6.08 | 1.81 |
| 16.31 | 5.44 | 0.98 |
| 16.73 | 5.30 | 10.96 |
| 18.63 | 4.76 | 15.05 |

TABLE 4-continued

| Pos. [°2θ] | d-spacing [Å] | Rel. Int. [%] |
|---|---|---|
| 18.77 | 4.73 | 18.31 |
| 19.10 | 4.65 | 4.90 |
| 19.79 | 4.49 | 0.90 |
| 21.49 | 4.14 | 9.97 |
| 22.53 | 3.95 | 8.53 |
| 24.89 | 3.58 | 0.83 |
| 26.98 | 3.30 | 0.29 |
| 28.95 | 3.08 | 1.91 |
| 29.43 | 3.04 | 0.73 |
| 32.95 | 2.72 | 0.59 |
| 35.22 | 2.55 | 0.48 |
| 38.10 | 2.36 | 0.65 |
| 39.39 | 2.29 | 0.38 |

Example 5~8: Preparation of Tosylate Form A (Slow Evaporation)

Appropriate amount of formula (I) tosylate solid was weighed into a 3-mL glass vial, and then corresponding solvent was added to dissolve the solid. The mixture was filtered into a new 3-mL glass vial using 0.45 μm PTFE filter membrane. The vial containing solution was sealed with parafilm, and the parafilm was pricked 3-4 holes. The solution was kept at room temperature or 50° C. for slow evaporation to obtain the solid.

The obtained solid was determined to be tosylate Form A after characterization. The detailed procedure was shown in Table 5, and the XRPD data of example 7 was summarized in Table 6.

TABLE 5

| | Mass | Solvent | | |
|---|---|---|---|---|
| Example | (mg) | Type (v/v) | Volume (mL) | Condition |
| 5 | 3.1 | Chloroform | 0.7 | Slow evaporation at RT |
| 6 | 3.1 | Dichloromethane | 0.7 | Slow evaporation at RT |
| 7 | 3.0 | Methanol/toluene (4/1) | 0.5 | Slow evaporation at RT |
| 8 | 3.1 | Tetrahydrofuran/ water (1/1) | 1.0 | Slow evaporation at 50° C. |

TABLE 6

| Pos. [°2θ] | d-spacing [Å] | Rel. Int. [%] |
|---|---|---|
| 6.22 | 14.21 | 83.47 |
| 9.27 | 9.55 | 42.34 |
| 9.53 | 9.28 | 3.30 |
| 12.47 | 7.10 | 1.59 |
| 13.36 | 6.63 | 7.44 |
| 14.06 | 6.30 | 41.61 |
| 14.56 | 6.09 | 10.12 |
| 15.69 | 5.65 | 4.49 |
| 16.38 | 5.41 | 21.85 |
| 16.73 | 5.30 | 18.08 |
| 18.28 | 4.85 | 19.75 |
| 18.63 | 4.76 | 100.00 |
| 18.81 | 4.72 | 25.37 |
| 19.10 | 4.65 | 35.30 |
| 19.30 | 4.60 | 19.91 |
| 19.76 | 4.49 | 27.92 |
| 20.56 | 4.32 | 9.24 |
| 21.07 | 4.22 | 14.35 |
| 21.48 | 4.14 | 30.83 |
| 22.52 | 3.95 | 35.91 |

TABLE 6-continued

| Pos. [°2θ] | d-spacing [Å] | Rel. Int. [%] |
|---|---|---|
| 22.98 | 3.87 | 3.63 |
| 23.38 | 3.80 | 4.52 |
| 23.73 | 3.75 | 3.38 |
| 24.87 | 3.58 | 7.69 |
| 25.34 | 3.52 | 4.07 |
| 26.24 | 3.40 | 2.14 |
| 26.76 | 3.33 | 12.58 |
| 27.09 | 3.29 | 7.77 |
| 27.50 | 3.24 | 7.44 |
| 28.11 | 3.18 | 3.67 |
| 28.53 | 3.13 | 4.75 |
| 28.95 | 3.08 | 7.48 |
| 29.38 | 3.04 | 5.96 |
| 30.15 | 2.96 | 2.27 |
| 30.62 | 2.92 | 1.58 |
| 31.24 | 2.86 | 2.62 |
| 31.95 | 2.80 | 2.29 |
| 32.39 | 2.76 | 1.32 |
| 32.86 | 2.73 | 3.73 |
| 34.15 | 2.63 | 0.81 |
| 37.12 | 2.42 | 1.36 |
| 37.94 | 2.37 | 1.85 |

Example 9: Preparation of Tosylate Form A (Slow Cooling)

Appropriate amount of formula (I) tosylate solid was weighed into a 3-mL glass vial, and then 0.5 mL of methanol was added to form a suspension. After the suspension was magnetically stirred at 50° C. (1000 rpm) for about two hours, the mixture was filtered into a new 3-mL glass vial using 0.45 μm PTFE filter membrane. The vial containing the solution was sealed, then cooled down to 5° C. from 50° C. at a rate of 0.1° C./min and kept at 5° C. to obtain solid.

The obtained solid was determined to be tosylate Form A after characterization. The XRPD data of example 9 was summarized in Table 7.

TABLE 7

| Pos. [°2θ] | d-spacing [Å] | Rel. Int. [%] |
|---|---|---|
| 6.22 | 14.21 | 100.00 |
| 9.27 | 9.54 | 14.44 |
| 13.38 | 6.62 | 3.07 |
| 14.15 | 6.26 | 6.33 |
| 14.56 | 6.08 | 4.21 |
| 15.74 | 5.63 | 1.29 |
| 16.40 | 5.40 | 4.54 |
| 16.75 | 5.29 | 9.40 |
| 18.39 | 4.82 | 6.01 |
| 18.63 | 4.76 | 28.56 |
| 18.78 | 4.72 | 27.10 |
| 19.10 | 4.65 | 16.85 |
| 19.41 | 4.57 | 4.30 |
| 19.84 | 4.48 | 7.03 |
| 20.62 | 4.31 | 2.45 |
| 21.15 | 4.20 | 5.63 |
| 21.50 | 4.13 | 12.62 |
| 22.52 | 3.95 | 19.82 |
| 23.43 | 3.80 | 1.48 |
| 24.92 | 3.57 | 2.93 |
| 26.82 | 3.32 | 2.83 |
| 27.59 | 3.23 | 1.95 |
| 28.65 | 3.12 | 3.41 |
| 28.94 | 3.08 | 4.93 |
| 29.38 | 3.04 | 2.89 |
| 30.26 | 2.95 | 1.01 |
| 31.33 | 2.86 | 1.41 |
| 32.02 | 2.80 | 1.03 |
| 32.90 | 2.72 | 3.57 |
| 33.99 | 2.64 | 1.46 |

TABLE 7-continued

| Pos. [°2θ] | d-spacing [Å] | Rel. Int. [%] |
|---|---|---|
| 38.04 | 2.37 | 1.49 |
| 39.39 | 2.29 | 1.52 |

Example 10~11: Preparation of Tosylate Form A (Rapid Cooling)

Appropriate amount of formula (I) tosylate solid was weighed into a 3-mL glass vial, and then corresponding solvent was added to form a suspension. After the suspension was magnetically stirred at 50° C. (1000 rpm) for about two hours, the mixture was filtered into a new 3-mL glass vial using 0.45 μm PTFE filter membrane. The vial containing solution was sealed and then kept under −20° C. for about 5 days, and the solid was obtained. If no solid was obtained after 10 mL of anti-solvent was added, the solution was evaporated at room temperature until the solid was obtained.

Figure 6:
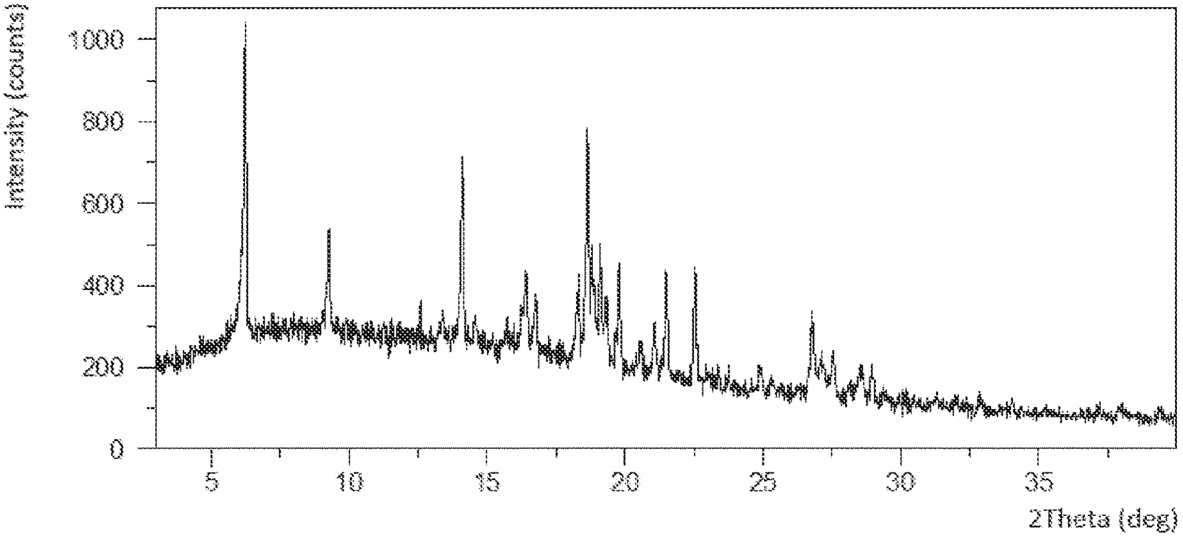
FIG. 6: XRPD pattern of tosylate Form A of example 11.

The obtained solid was determined to be tosylate Form A after characterization. The detailed procedure was shown in Table 8. The XRPD pattern of example 11 was shown in FIG. 6, and the corresponding XRPD data was summarized in Table 9.

TABLE 8

| Example | Mass (mg) | Solvent (v/v) | Volueme (mL) | Condition |
|---|---|---|---|---|
| 10 | 10.2 | Ethanol | 1.0 | Kept under −20° C. |
| 11 | 10.4 | Methanol/acetone (1/1) | 1.0 | Kept under −20° C. |

TABLE 9

| Pos. [°2θ] | d-spacing [Å] | Rel. Int. [%] |
|---|---|---|
| 6.22 | 14.20 | 100.00 |
| 9.27 | 9.54 | 32.41 |
| 13.36 | 6.63 | 8.16 |
| 14.08 | 6.29 | 59.96 |
| 14.55 | 6.09 | 9.57 |
| 15.70 | 5.64 | 8.23 |
| 16.40 | 5.41 | 26.01 |
| 16.74 | 5.30 | 18.72 |
| 18.30 | 4.85 | 23.53 |
| 18.64 | 4.76 | 74.69 |
| 18.86 | 4.71 | 25.15 |
| 19.10 | 4.65 | 37.16 |
| 19.31 | 4.60 | 22.00 |
| 19.77 | 4.49 | 33.19 |
| 20.57 | 4.32 | 7.83 |
| 21.08 | 4.21 | 17.05 |
| 21.49 | 4.14 | 34.43 |
| 22.53 | 3.95 | 34.55 |
| 23.38 | 3.80 | 4.92 |
| 24.90 | 3.58 | 6.73 |
| 26.77 | 3.33 | 21.88 |
| 27.11 | 3.29 | 12.14 |
| 27.52 | 3.24 | 12.31 |
| 28.56 | 3.13 | 9.71 |
| 28.97 | 3.08 | 8.94 |
| 32.86 | 2.73 | 3.38 |
| 37.94 | 2.37 | 2.82 |
| 39.39 | 2.29 | 3.19 |

Example 12~19: Preparation of Tosylate Form A (Anti-solvent Addition)

Appropriate amount of formula (I) tosylate solid was weighed into a 20-mL glass vial, and then corresponding solvent was added to form a clear solution. Anti-solvent was added into the solution dropwise with magnetically stirring (1000 rpm). The solid was obtained by centrifugal separation. If no solid was obtained after 10 mL of anti-solvent was added, the solution was evaporated at room temperature until the solid was obtained.

The obtained solid was determined to be tosylate Form A after characterization. The detailed procedure was shown in Table 10. The XRPD data of example 13 was summarized in Table 11.

TABLE 10

| | | Solvent | | Anti-solvent | | |
|---|---|---|---|---|---|---|
| Example | Mass (mg) | Type | Volume (mL) | Type | Volume (mL) | Condition |
| 12 | 15.1 | Methanol | 1.5 | Isopropyl acetate | 10.0 | Precipitation |
| 13 | 14.7 | Methanol | 1.5 | Methyl tert-butyl ether | 4.5 | Precipitation |
| 14 | 14.6 | Dichloromethane | 2.0 | Ethyl acetate | 10.0 | Precipitation |
| 15 | 14.8 | Dichloromethane | 2.0 | Tetrahydrofuran | 10.0 | Precipitation |
| 16 | 14.7 | Dichloromethane | 2.0 | n-Heptane | 2.2 | Precipitation |
| 17 | 14.9 | Dichloromethane | 2.0 | Toluene | 3.8 | Precipitation |
| 18 | 15.0 | Dimethylsulfoxide | 0.3 | Acetone | 5.0 | Precipitation |
| 19 | 14.9 | Dimethylacetamide | 0.7 | Isopropanol | 10.0 | Precipitation |

TABLE 11

| Pos. [°2θ] | d-spacing [Å] | Rel. Int. [%] |
|---|---|---|
| 6.22 | 14.21 | 100.00 |
| 9.27 | 9.54 | 15.93 |
| 14.06 | 6.30 | 1.45 |
| 14.56 | 6.08 | 3.01 |
| 16.73 | 5.30 | 2.57 |
| 18.63 | 4.76 | 23.36 |
| 18.80 | 4.72 | 13.59 |
| 19.10 | 4.65 | 8.31 |
| 19.75 | 4.49 | 1.01 |
| 21.49 | 4.14 | 3.26 |
| 22.52 | 3.95 | 9.05 |

Example 20~24: Preparation of Tosylate Form A (Reserve Anti-solvent Addition Appropriate amount of formula (I) tosylate solid was weighed into a 5-mL glass vial, and then corresponding solvent was added to form a clear solution. Anti-solvent was added into a 20-mL glass vial with magnetically stirring (1000 rpm), and then the clear solution was added quickly into the 20-mL glass vial. If no precipitation was obtained, the solution was kept under −20° C. until the solid was obtained.

Figure 7:
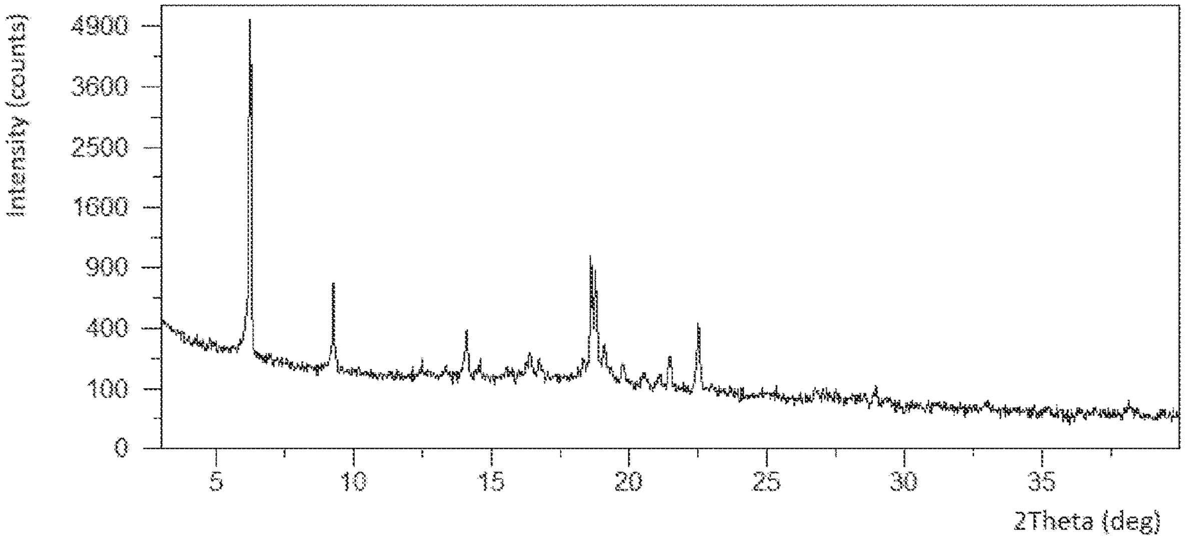
FIG. 7: XRPD pattern of tosylate Form A of example 23.

The obtained solid was determined to be tosylate Form A after characterization. The detailed procedure was shown in Table 12. The XRPD pattern of example 23 was shown in FIG. 7 and the corresponding XRPD data was summarized in Table 13.

TABLE 12

| | | Solvent | | Anti-solvent | | |
|---|---|---|---|---|---|---|
| Example | Mass (mg) | Type | Volueme (mL) | Type | Volueme (mL) | Condition |
| 20 | 9.4 | Dichloromethane | 2.0 | Isopropyl acetate | 10.0 | Precipitated after |
| 21 | 9.6 | Dimethylacetamide | 0.5 | Methyl tert-butyl ether | 4.0 | adding anti-solvent |
| 22 | 9.6 | Dichloromethane | 2.0 | Toluene | 10.0 | Precipitated after |
| 23 | 9.6 | Dimethylacetamide | 0.5 | 2-Methyl tetrahydrofuran | 4.0 | being kept under −20° C. |
| 24 | 10.1 | Dimethylacetamide | 0.5 | Isopropanol | 4.0 | |

TABLE 13

| Pos. [°2θ] | d-spacing [Å] | Rel. Int. [%] |
|---|---|---|
| 6.22 | 14.21 | 100.00 |
| 9.27 | 9.54 | 11.35 |
| 12.44 | 7.11 | 0.77 |
| 13.36 | 6.62 | 0.67 |
| 14.09 | 6.28 | 4.74 |
| 14.60 | 6.06 | 0.91 |
| 15.57 | 5.69 | 0.57 |
| 15.73 | 5.63 | 0.53 |
| 16.38 | 5.41 | 2.33 |
| 16.73 | 5.29 | 1.50 |
| 17.08 | 5.19 | 0.54 |
| 18.32 | 4.84 | 1.40 |
| 18.63 | 4.76 | 18.29 |
| 18.79 | 4.72 | 14.98 |
| 19.10 | 4.65 | 3.81 |
| 19.79 | 4.49 | 1.90 |
| 20.56 | 4.32 | 0.78 |
| 21.11 | 4.21 | 0.85 |
| 21.49 | 4.14 | 2.96 |
| 22.52 | 3.95 | 6.01 |

TABLE 13-continued

| Pos. [°2θ] | d-spacing [Å] | Rel. Int. [%] |
|---|---|---|
| 28.95 | 3.08 | 0.64 |
| 38.15 | 2.36 | 0.28 |

Example 25~31: Preparation of Tosylate Form A (Polymer-induced Crystallization)

Appropriate amount of formula (I) tosyalate solid was weighed into a 3-mL glass vial, and then corresponding solvent was added to form a clear solution. The mixture was filtered into a new 3-mL glass vial using 0.45 μm PTFE filter membrane. The solution was evaporated at room temperature.

The obtained solid was determined to be tosylate Form A after characterization. The detailed procedure was shown in Table 14. The XRPD data of example 27 was summarized in Table 15.

TABLE 14

| Example | Mass (mg) | Solvent | Volume (mL) | Polymers | Condition |
|---|---|---|---|---|---|
| 25 | 4.6 | Dichloromethane | 1.0 | PVPK13-18 | Evaporation |
| 26 | 4.5 | Chloroform | 1.0 | PVP 407 | Evaporation |
| 27 | 4.8 | Dichloromethane | 1.0 | Methylcellulose | Evaporation |
| 28 | 4.9 | Methanol | 1.0 | Polyvinyl alcohol 1799 | Evaporation |
| 29 | 4.8 | Dichloromethane | 1.0 | Acrylic resinL 100 | Evaporation |
| 30 | 4.5 | Chloroform | 1.0 | Carboxyl methyl cellulose | Evaporation |
| 31 | 4.8 | Chloroform | 1.0 | Hydroxypropyl-β-cyclodextrin | Evaporation |

TABLE 15

| Pos. [°2θ] | d-spacing [Å] | Rel. Int. [%] |
|---|---|---|
| 6.22 | 14.21 | 100.00 |
| 9.26 | 9.55 | 38.76 |
| 13.34 | 6.63 | 8.89 |
| 14.07 | 6.30 | 46.42 |
| 14.52 | 6.10 | 9.41 |
| 15.66 | 5.66 | 8.51 |
| 16.37 | 5.42 | 21.41 |
| 16.73 | 5.30 | 23.13 |
| 18.27 | 4.86 | 20.21 |
| 18.63 | 4.76 | 85.56 |
| 18.79 | 4.72 | 29.33 |
| 19.10 | 4.65 | 44.58 |
| 19.25 | 4.61 | 19.76 |
| 19.77 | 4.49 | 27.56 |
| 20.53 | 4.32 | 11.38 |
| 21.07 | 4.22 | 15.74 |
| 21.48 | 4.14 | 37.69 |
| 22.52 | 3.95 | 42.68 |
| 23.35 | 3.81 | 7.39 |
| 24.85 | 3.58 | 8.79 |
| 25.32 | 3.52 | 4.29 |
| 26.77 | 3.33 | 13.55 |
| 27.11 | 3.29 | 11.29 |
| 27.51 | 3.24 | 8.44 |
| 28.38 | 3.14 | 8.65 |
| 28.54 | 3.12 | 8.82 |
| 28.95 | 3.08 | 11.19 |
| 29.35 | 3.04 | 6.68 |

Example 32~38: Preparation of Tosylate Form A (Fast Evaporation)

Appropriate amount of formula (I) tosylate solid was weighed into a 3-mL glass vial, and corresponding solvent was added to dissolve the solid. The mixture was filtered into a new 3-mL glass vial using 0.45 μm PTFE filter membrane. The solution was evaporated at 50° C. or 5° C.

The obtained solid was determined to be tosylate Form A after characterization. The detailed procedure was shown in Table 16. The XRPD data of example 33 was summarized in Table 17.

TABLE 16

| Example | Mass (mg) | Solvent (v/v) | Volume (mL) | Temp (° C.) | Condition |
|---|---|---|---|---|---|
| 32 | 4.6 | Dimethylacetamide | 0.5 | 50 | Evaporation |
| 33 | 5.1 | Chloroform | 0.5 | 50 | Evaporation |
| 34 | 4.7 | Water | 0.5 | 50 | Evaporation |
| 35 | 4.5 | Isopropanol/ Methanol (4/1) | 1.0 | 50 | Evaporation |
| 36 | 5.7 | Toluene/ dichloromethane (1/1) | 1.0 | 50 | Evaporation |
| 37 | 5.1 | Ethanol | 1.0 | 5 | Evaporation |
| 38 | 4.4 | Acetone/ Methanol (4/1) | 1.0 | 5 | Evaporation |

TABLE 17

| Pos. [°2θ] | d-spacing [Å] | Rel. Int. [%] |
|---|---|---|
| 6.22 | 14.21 | 100.00 |
| 9.27 | 9.54 | 31.72 |
| 12.45 | 7.10 | 2.72 |
| 13.35 | 6.63 | 5.68 |
| 14.07 | 6.29 | 45.06 |
| 14.56 | 6.08 | 4.18 |
| 15.70 | 5.64 | 6.05 |
| 16.38 | 5.41 | 25.53 |

TABLE 17-continued

| Pos. [°2θ] | d-spacing [Å] | Rel. Int. [%] |
|---|---|---|
| 16.74 | 5.29 | 13.33 |
| 18.29 | 4.85 | 22.22 |
| 18.64 | 4.76 | 56.62 |
| 19.10 | 4.65 | 28.22 |
| 19.30 | 4.60 | 19.04 |
| 19.77 | 4.49 | 25.08 |
| 20.54 | 4.32 | 7.33 |
| 21.08 | 4.22 | 15.29 |
| 21.49 | 4.14 | 26.77 |
| 22.52 | 3.95 | 22.76 |
| 24.91 | 3.58 | 4.98 |
| 26.77 | 3.33 | 12.69 |
| 27.06 | 3.29 | 8.17 |
| 27.51 | 3.24 | 7.64 |
| 28.54 | 3.13 | 5.88 |
| 28.97 | 3.08 | 5.87 |

Example 39: Stability Study

Figure 10:
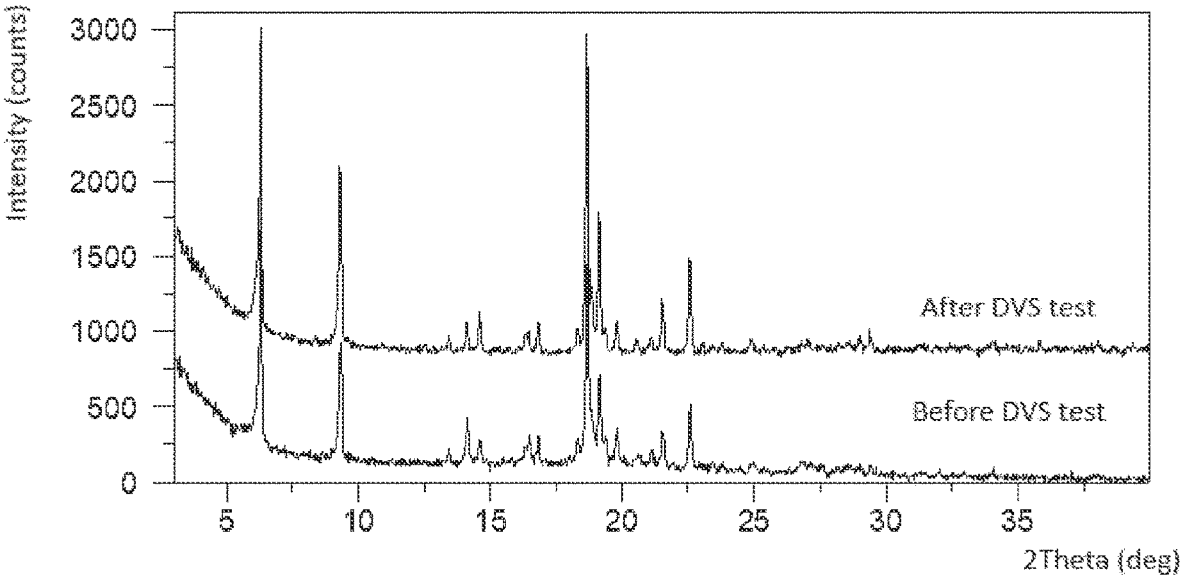
FIG. 10: XRPD pattern overlay of tosylate Form A before and after DVS test of example 40.

Approximately 10 mg of tosylate Form A were stored under different conditions of 25° C./60% RH and 40° C./75% RH. XRPD and chemical impurity were checked at 1 week, 2 weeks, 4 weeks and 8 weeks. The results were summarized in Table 18 and the XRPD overlay was shown in FIG. 10.

TABLE 18

| Stability study | | | |
|---|---|---|---|
| Time point (week) | Condition | Solid form | Puriy (%) |
| 1 week | 25° C./60% RH | A | 99.92 |
| 2 weeks | | A | 100.0 |
| 4 weeks | | A | 99.89 |
| 8 weeks | | A | 99.92 |
| 1 week | 40° C./75% RH | A | 99.90 |
| 2 weeks | | A | 99.91 |
| 4 weeks | | A | 99.90 |
| 8 weeks | | A | 99.91 |

Based on the above results, tosylate Form A kept stable for at least 8 weeks. Crystalline state of Form A doesn't change, and the chemical purity is above 99%. tosylate Form A of present disclosure showed good physical/chemical stability under 25° C./60% RH and 40° C./75%.

Example 40: Hygroscopicity Study

Figure 8:
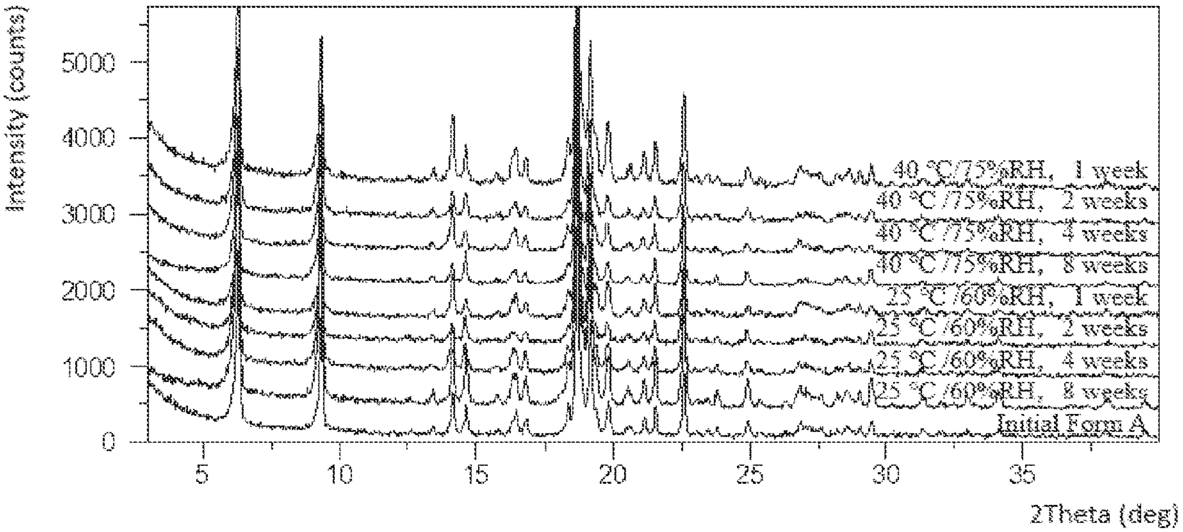
FIG. 8: XRPD pattern overlay of tosylate Form A before and after stability experiments of example 39.
Figure 9:
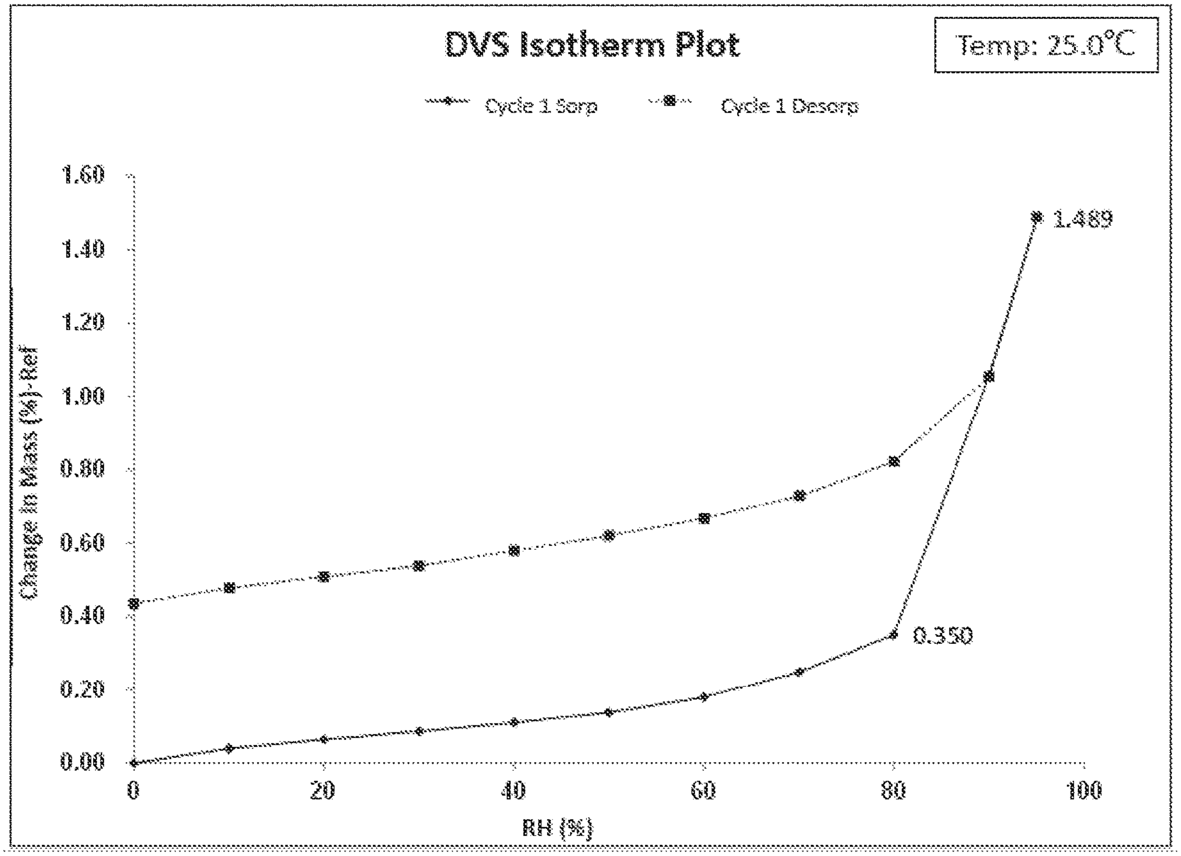
FIG. 9: DVS plot of tosylate Form A of example 40.

Dynamic vapor sorption (DVS) was applied to test hygroscopicity of tosylate Form A solid and solid in the prior art with about 10 mg of samples. XRPD patterns were collected. The DVS plot of tosylate Form A was shown in FIG. 8, and no obvious form change was observed after DVS test (FIG. 9). As a result, DVS plot showed a weight gain of 0.35% at 80% RH, indicating tosylate Form A was slightly hygroscopic. Compared with the prior art, tosylate Form A showed relatively lower hygroscopicity, which could well meet the requirements of pharmaceutical production and use.

Description and Definition of Hygroscopicity (Chinese Pharmacopoeia 2015 Edition Appendix XIX J Guidance for Hygroscopicity Evaluation)

Deliquescent: sufficient water is absorbed to form a liquid

Very hygroscopic: increase in mass is equal to or greater than 15 percent

Hygroscopic: increase in mass is less than 15 percent and equal to or greater than 2 percent Slightly hygroscopic: increase in mass is less than 2 percent and equal to or greater than 0.2 percent Non-hygroscopic or almost non hygroscopic: increase in mass is less than 0.2 percent.

Example 41: Solubility of Crystalline Form

Tosylate Form A and solid in the prior art were suspended into SGF, FaSSIF, FeSSIF and water to get saturated solutions. After equilibrated for 1 hour, 2 hours, 4 hours and 24 hours, concentrations of the saturated solutions were measured by HPLC. The results were summarized in Table 19. The results show that the solubility of tosylate Form A is higher than that of solid in the prior art, which meets the solubility requirement of oral administration drugs and has better application prospect.

TABLE 19

| Media | 1 hr (mg/mL) | 2 hr (mg/mL) | 4 hr (mg/mL) | 24 hr (mg/mL) |
|---|---|---|---|---|
| $H_2O$ | 5.2622 | 5.3388 | 5.2410 | 5.5622 |
| SGF | 5.5375 | 5.9864 | 5.0784 | 5.6942 |
| FaSSIF | 7.1155 | 7.3099 | 7.2968 | 7.5385 |
| FeSSIF | 6.7660 | 7.0277 | 7.3408 | 7.7836 |

Example 42: Compressibility of Crystalline Form

A manual tablet press was used for tabletting. Appropriate amount of tosylate Form A and solid in the prior art were compressed by circle punches under 350 MPa pressure to form a tablet. Hardness (H) of the tablet was determined to be 18.36 N by a tablet hardness tester. Diameter (D) and thickness (L) of the tablet were determined to be 6 mm and 1.02 mm by a vernier caliper, respectively. The tensile strength of the tablets was calculated to be 1.9 MPa through the equation of $T=2H/\pi DL$. As a result, tosylate Form A showed a good compressibility, which meets the requirement of formulation process.

Example 43: Intrinsic Dissolution of Crystalline Form

Approximately 100 mg of tosylate Form A and the solid in the prior art were added into the cavity of the die, and then compressed at 5 KN and held for 1 minute to obtain a tablet having a surface area of 0.5 $cm^2$. Intrinsic dissolution experiment was performed on the tablets, and the corresponding condition was shown in Table 20. As a result, tosylate Form A showed a higher dissolution rate than the solid in the prior art.

TABLE 20

| Dissolution apparatus | Agilent 708DS |
|---|---|
| Method | Paddle |
| Media | pH 6.8 phosphate buffer solution |
| Media volume | 900 mL |
| Stirring rate | 75 rpm |
| Temperature | 37° C. |
| Sampling time | 1, 2, 3, 4, 5, 10, 15, 20, 25, 30 mins |
| Media addition | No |

Example 44: Crystal Habit

Figure 11:
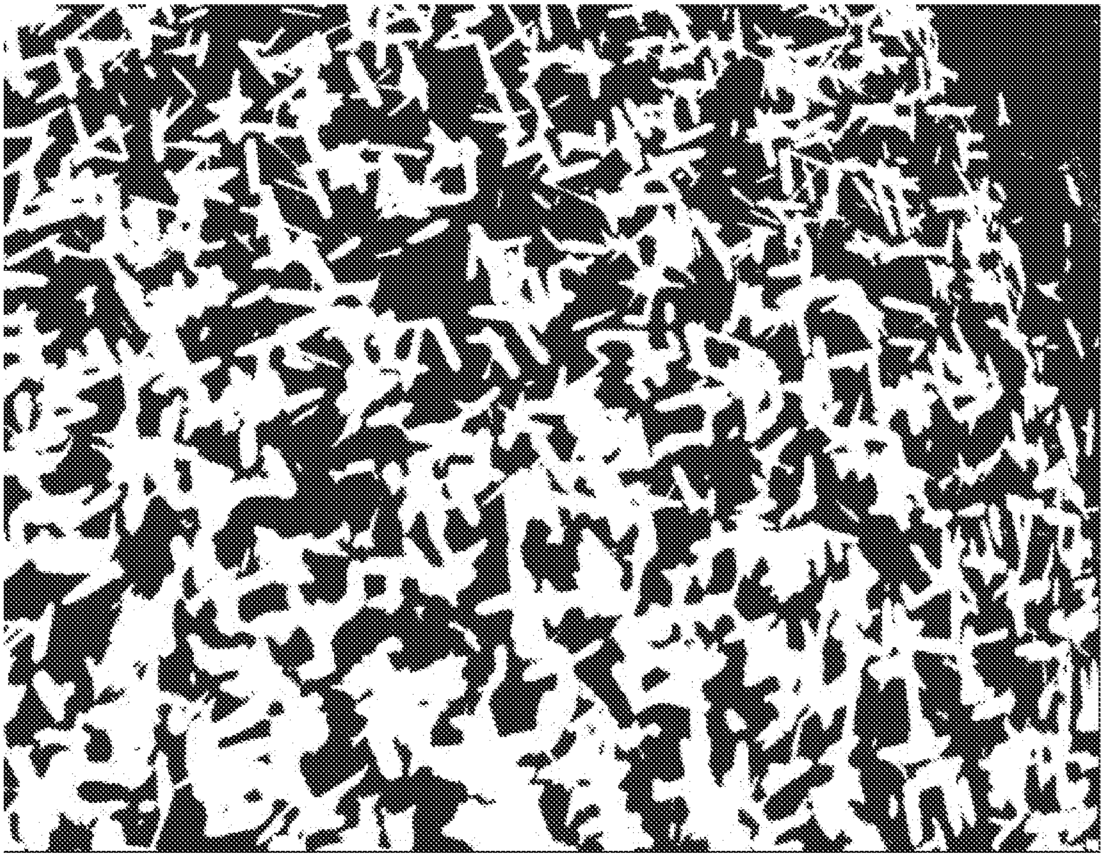
FIG. 11: PLM image of tosylate Form A of example 44.

Polarized light microscopy was used to observe the crystal habit of the particles of tosylate Form A. As a result, tosylate Form A was composed of rod-like particles, with good flowability (FIG. 11).

Example 45: PSD Test

Approximately 10-30 mg of tosylate Form A solid was added into 10 mL of Isopar G (containing 0.2% lecithin). The mixture was mixed thoroughly and transferred into the SDC. The experiment was started when the obscuration is in appropriate range. The particle size distribution (PSD) was tested before and after 30 seconds of ultrasound. As a result, tosylate Form A showed a unimodal distribution with a mean particle size (MV) of 400 μm. Also, no obvious change or agglomeration was observed after sonication, indicating tosylate Form A has good dispersion. Compared to prior art solid, the particle size distribution of tosylate Form A is uniform, which is superior to that of solid in the prior art.

Example 46: Adhesiveness Propensity Study

Approximately 30 mg of tosylate Form A and the solid in the prior art were weighed and then added into the dies of 8 mm round tooling, compressed at 10 kN pressure and held for 30 s. The punch was weighed and amount of material sticking to the punch was calculated. The compression was repeated once and the cumulative amount, maximum amount and average amount of material sticking to the punch during the compression were recorded. As a result, the adhesiveness of tosylate Form A is superior to the prior art solid.

The above-mentioned embodiments are only intended to illustrate the technical concept and characteristics of the present disclosure, and the purpose thereof is to enable those who are familiar with the art to understand the content of the present disclosure and implement them accordingly, and cannot limit the protection scope of the present disclosure. All equivalent changes or modifications made according to the spirit of the present disclosure should be included within the protection scope of the present disclosure.

What is claimed is:

1. A crystalline Form A of a tosylate of a compound of formula (I) ((1S)-2,2-difluorocyclo-propyl) ((1R,5S)-3-(2-((1-methyl-1H-pyrazol-4-yl)amino)pyrimidin-4-yl)-3,8-diazabicyclo[3.2.1]octan-8-yl)methanone, wherein the crystalline Form A is characterized by a reflection X-ray powder diffraction pattern (Cu-Kα radiation) comprising characteristic diffraction peaks at angles (2θ) of 6.2°±0.2° 2θ, 9.3°±0.2° 2θ, and 18.6°±0.2° 2θ, Formula (I)

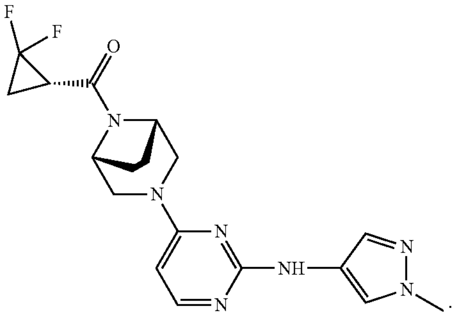
.

2. A process for preparing the crystalline Form A according to claim 1, wherein the process comprises, Formula (I)

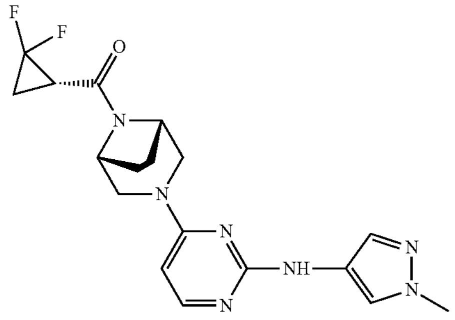

dissolving formula (I) tosylate into a solvent, filtering, and quickly adding the filtrate into an anti-solvent to obtain the crystalline Form A.

3. A pharmaceutical composition, wherein said pharmaceutical composition comprises the crystalline Form A according to claim 1 and pharmaceutically acceptable carriers.

* * * * *